(12) United States Patent
Torrence et al.

(10) Patent No.: US 9,216,936 B2
(45) Date of Patent: Dec. 22, 2015

(54) PROCESS FOR RECOVERING HALOGEN PROMOTERS AND REMOVING PERMANGANATE REDUCING COMPOUNDS

(75) Inventors: G. Paull Torrence, League City, TX (US); Raymond Zinobile, Houston, TX (US); Oyeyemi Oyerinde, Houston, TX (US)

(73) Assignee: Celanese International Corporation, Irving, TX (US)

( * ) Notice: Subject to any disclaimer, the term of this patent is extended or adjusted under 35 U.S.C. 154(b) by 719 days.

(21) Appl. No.: 13/272,762

(22) Filed: Oct. 13, 2011

(65) Prior Publication Data

US 2012/0090980 A1  Apr. 19, 2012

Related U.S. Application Data

(60) Provisional application No. 61/392,736, filed on Oct. 13, 2010.

(51) Int. Cl.
*C07C 51/48* (2006.01)
*C07C 51/12* (2006.01)
*B01D 3/14* (2006.01)
*C07C 51/44* (2006.01)

(52) U.S. Cl.
CPC .............. *C07C 51/12* (2013.01); *B01D 3/143* (2013.01); *C07C 51/44* (2013.01); *C07C 51/48* (2013.01)

(58) Field of Classification Search
CPC ................................ C07C 51/44; C07C 51/48
See application file for complete search history.

(56) References Cited

U.S. PATENT DOCUMENTS

| | | |
|---|---|---|
| 3,769,329 A | 10/1973 | Paulik et al. |
| 4,615,806 A | 10/1986 | Hilton |
| 4,894,477 A | 1/1990 | Scates et al. |
| 4,908,477 A | 3/1990 | Hartmann et al. |
| 5,001,259 A | 3/1991 | Smith et al. |
| 5,026,908 A | 6/1991 | Smith et al. |
| 5,144,068 A | 9/1992 | Smith et al. |
| 5,696,284 A | 12/1997 | Baker et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 6,143,930 A | 11/2000 | Singh et al. |
| 6,225,498 B1 | 5/2001 | Blay et al. |
| 6,339,171 B1 | 1/2002 | Singh et al. |
| 6,627,770 B1 | 9/2003 | Cheung et al. |
| 7,005,541 B2 | 2/2006 | Cheung et al. |
| 7,223,886 B2 | 5/2007 | Scates et al. |
| 8,076,507 B2 * | 12/2011 | Scates et al. .................. 562/519 |
| 2006/0247466 A1 | 11/2006 | Zinobile et al. |
| 2009/0270651 A1 | 10/2009 | Zinobile et al. |

FOREIGN PATENT DOCUMENTS

| | | |
|---|---|---|
| CN | 1926087 | 3/2007 |
| CN | 101163658 | 4/2008 |
| WO | WO 92/06062 A1 | 4/1992 |
| WO | WO 2010/053571 A2 | 5/2010 |

OTHER PUBLICATIONS

Treybal, Liquid Extraction, 2nd Ed., McGraw-Hill Book Company, New York, NY, 1963, pp. 349-366.*
Jones, J. H.., (2000), "The Cativa Process for the Manufacture of Acetic Acid", Platinum Metals Review, 44 (3): 94-105.
International Search Report and Written Opinion mailed Dec. 7, 2012 in corresponding International Application No. PCT/US2011/056136.
International Search Report and Written Opinion mailed Dec. 7, 2012 in corresponding International Application No. PCT/US2011/056139.
Office Action for Chinese Appl. No. 201180049260.2 dated Aug. 5, 2014.
Office Action for corresponding U.S. Appl. No. 13/272,747 dated Jul. 22, 2014.
Response to Office Action for corresponding U.S. Appl. No. 13/272,747, filed Oct. 22, 2014.
Office Action for corresponding Chinese Appl. No. 201180049274.4 dated May 30, 2014.

* cited by examiner

*Primary Examiner* — Paul A Zucker

(57) ABSTRACT

This invention relates to processes for producing acetic acid and, in particular, to improved processes for recovering $C_{2+}$ alkyl halides and removing permanganate reducing compounds formed during the carbonylation of methanol in the presence of a Group VIII metal carbonylation catalyst to produce acetic acid.

19 Claims, 2 Drawing Sheets

PROCESS FOR RECOVERING HALOGEN PROMOTERS AND REMOVING PERMANGANATE REDUCING COMPOUNDS

FIELD OF THE INVENTION

This invention relates to processes for producing acetic acid and, in particular, to improved processes for recovering halogen promoters, namely methyl iodide, and removing permanganate reducing compounds formed during the carbonylation of methanol in the presence of a Group VIII metal carbonylation catalyst to produce acetic acid.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "The Cativa™ Process for the Manufacture of Acetic Acid," *Platinum Metals Review*, 44 (3): 94-105, the entire content and disclosure of which is hereby incorporated by reference.

The crude acetic acid product from the reactor is processed in a purification section to remove impurities and recover acetic acid. These impurities, which may be present in trace amounts, affect the quality of acetic acid, especially as the impurities are circulated through the reaction process, which, among other things, can result in the build up of these impurities over time. Conventional purification techniques to remove these impurities include treating the acetic acid product streams with oxidizers, ozone, water, methanol, activated-carbon, amines, and the like. The treatments may also be combined with the distillation of the crude acetic acid product. However, the additional treatment of the final product adds cost to the process, and distillation of the treated acetic acid product can result in additional impurities being formed.

Processes for removing these impurities may also remove compounds in the reaction medium, such as the halogen promoter. Several processes have been taught for recovering the halogen promoter including treatment of vented streams and extraction.

Treatment of vented streams allows recovery of halogen promoters. For example, U.S. Publication No. 2009/0270651 discloses a methanol carbonylation system that includes an absorber tower adapted for receiving a vent gas stream and removing methyl iodide therefrom with a scrubber solvent, the absorber tower being coupled to first and second scrubber solvent sources which are capable of supplying different first and second scrubber solvents. A switching system including valves alternatively provides first or second scrubber solvents to the absorber tower and returns the used solvent and absorbed material to the carbonylation system to accommodate different operating modes.

Extraction may also recover halogen promoters from the carbonylation products. For example, U.S. Pat. No. 4,908,477 discloses separating organic iodine compounds from carbonylation products of methanol, methyl acetate and dimethyl ether and from mixtures of such carbonylation products by a process wherein the iodine compounds are removed by liquid phase extraction with a non-aromatic hydrocarbon.

The methods for recovering halogen promoters are not able to remove other impurities. In particular, the impurities that decrease the permanganate time of the acetic acid are not removed when recovering halogen promoters. Permanganate time is a quality test commonly used in the acetic acid industry to determine the amount of impurities present in an acetic acid product. These impurities include saturated and unsaturated carbonyl compounds, generally referred to as permanganate reducing compounds (PRC's). PRC's, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. These compounds are removed through one or more columns and extraction units.

The art has disclosed that PRC's present in the crude acetic acid product streams generally concentrate in the overhead stream from the light ends column. Accordingly, the light ends column overhead stream has been treated with an amine compound (such as hydroxylamine), which reacts with the carbonyl compounds to form derivatives that can be separated from the remaining overhead stream by distillation, resulting in an acetic acid product with improved permanganate time.

It has been disclosed in U.S. Pat. Nos. 6,143,930 and 6,339,171, the entireties of which are incorporated herein by reference, that it is possible to significantly reduce undesirable impurities in the acetic acid product by performing a multi-stage purification on the light ends column overhead stream. These patents disclose a purification process in which the light ends overhead stream is distilled twice, in each case taking the acetaldehyde overhead and returning a methyl iodide-rich residue to the reactor. The acetaldehyde-rich distillate obtained after the two distillation steps is optionally extracted with water to remove the majority of the acetaldehyde for disposal, leaving a significantly lower acetaldehyde concentration in the raffinate that is recycled to the reactor.

In addition, it has been disclosed in US Pub. No. 2006/0247466, the entirety of which is incorporated herein by reference, that it is possible to reduce undesirable impurities in the acetic acid product by subjecting the light ends overhead stream to a single distillation to obtain an overhead stream. The overhead stream is then subjected to an extraction that selectively removes and/or reduces PRC's.

U.S. Pat. No. 7,223,886, the entirety of which is incorporated herein by reference, discloses a method for reducing the formation of alkyl iodides and $C_3$ to $C_8$ carboxylic acids by removing PRC's from the light phase of the condensed light ends overhead stream, including (a) distilling the light phase to yield a PRC enriched overhead stream; and (b) extracting the overhead stream with water in at least two consecutive stages and separating therefrom one or more aqueous streams containing PRC's.

The effluent of the extraction units comprises the PRC's that are removed from the acetic acid production process. The effluent may also comprise impurities that may result in a loss of the compounds in the reactor and result in effluent streams that are more expensive and difficult to treat.

While the above-described processes have been successful in reducing and/or removing PRC's from the carbonylation system, further improvements can still be made for recovering the halogen promoters.

SUMMARY OF THE INVENTION

In one embodiment, the present invention is directed to a process for removing permanganate reducing compounds (PRC's) from a crude acetic acid composition, the process comprising the steps of separating the crude acetic acid composition in a light ends column into an overhead vapor stream comprising halogen promoter, water, acetic acid, methyl acetate and at least one PRC, and an acetic acid product stream; condensing and biphasically separating the overhead vapor stream into a heavy phase and a light phase; separating the light phase in a distillation column into an overhead PRC stream and a bottoms stream, wherein the overhead PRC stream is enriched with PRC with respect to the bottoms stream; condensing the overhead PRC stream and extracting in a first extractor the condensed overhead PRC stream to obtain a first aqueous stream comprising water, halogen promoter and at least one PRC, and a first raffinate comprising methyl acetate; and extracting in a second extractor the first aqueous stream to obtain a second raffinate comprising water, and at least one PRC, and an extract stream comprising halogen promoter, and a second extractant.

In another embodiment, the present invention is directed to a process for removing permanganate reducing compounds (PRC's) from a crude acetic acid composition, the process comprising the steps of separating the crude acetic acid composition in a light ends column into an overhead vapor stream comprising halogen promoter, water, acetic acid, methyl acetate and at least one PRC, and an acetic acid product stream; condensing and biphasically separating the overhead vapor stream into a heavy phase and a light phase; separating the light phase in a distillation column into an overhead PRC stream and a bottoms stream, wherein the overhead PRC stream is enriched with PRC with respect to the bottoms stream; condensing the overhead PRC stream and extracting in a first extractor the condensed overhead PRC stream to obtain a first aqueous stream comprising water, halogen promoter and at least one PRC, and a first raffinate comprising methyl acetate; extracting in a second extractor the first aqueous stream to obtain a second raffinate comprising water, and at least one PRC, and an extract stream comprising halogen promoter, and a second extractant; separating the extract stream in a recovery column to produce a residue comprising the second extractant, and a distillate comprising the halogen promoter; and introducing at least a portion of the distillate to a carbonylation reactor for producing the crude acetic acid composition.

BRIEF DESCRIPTION OF DRAWINGS

The present invention will be better understood in view of the appended non-limiting figures, wherein.

DETAILED DESCRIPTION OF THE INVENTION

Figure 1:
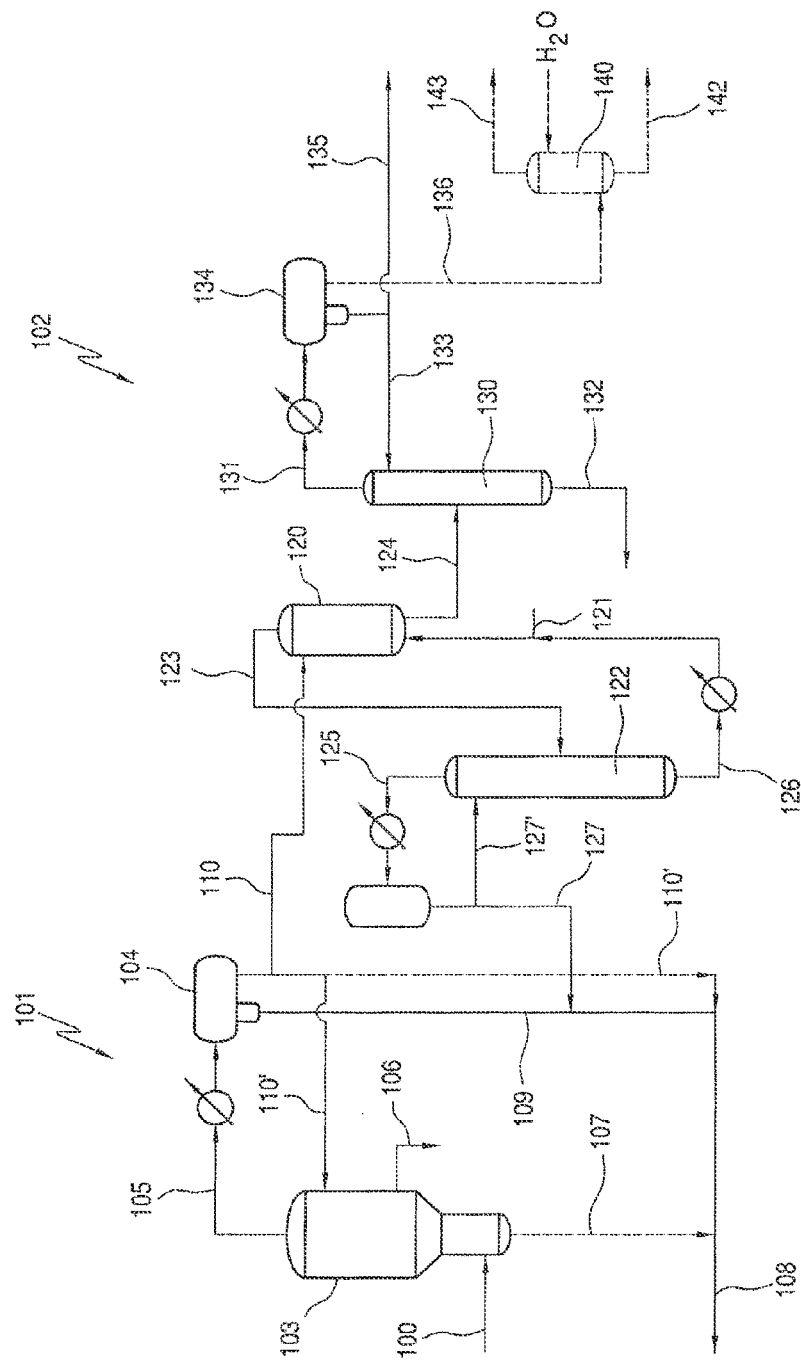
FIG. 1 illustrates an exemplary PRC removal system (PRS) that recovers halogen promoters from the feed to the PRS according to one embodiment of the invention.

The present invention generally relates to recovery of halogen promoters when removing PRC's, such as acetaldehyde, from the carbonylation process. In preferred embodiments, the halogen promoter is methyl iodide (MeI). When removing PRC's, the halogen promoters may pass through into purge streams that are not returned to the carbonylation reactor. Although the amount of halogen promoters in the purge streams may be relatively small, the cost associated with purging the halogen promoters may be significant. Embodiments of the present invention advantageously increase the amounts of halogen promoters that may be recovered thereby reducing costs, improving efficiency and reducing the need to treat purge streams.

In one embodiment, in addition to the recovery of halogen promoters, the processes of the present invention may further remove $C_{2+}$ alkyl halides. As a result of the byproducts formed during the carbonylation reaction, especially acetaldehyde, other $C_{2+}$ alkyl halides, such as ethyl iodide, propyl iodide, butyl iodide, pentyl iodide, hexyl iodide, and other $C_{2+}$ alkyl halides and isomers thereof, may also build up in the process. $C_{2+}$ alkyl halides generally refer to halides that are not halogen promoters. The halogen promoters and the $C_{2+}$ alkyl halides may cause corrosion in the system by forming hydroiodic acid in distillation portions of the PRS as described in several reactions that involve the halogen promoter, methyl iodide. As an example:

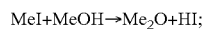

MeI+MeOH→Me$_2$O+HI;

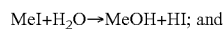

MeI+H$_2$O→MeOH+HI; and

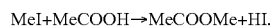

MeI+MeCOOH→MeCOOMe+HI.

While not being bound to one particular theory, the removal of the halogen promoters and these $C_{2+}$ alkyl halides prior to removing PRC's will preclude the formation of HI and therefore decrease general corrosion and reduce polymerization of PRC's catalyzed by HI, in particular, acetaldehyde, in the distillation process. Unless the $C_{2+}$ alkyl halides are removed, these compounds will be entrained with the acetic acid product and must be removed after the distillation using, for example, one or more guard beds. Embodiments of the present invention advantageously remove these $C_{2+}$ alkyl halides while recovering the halogen promoter, namely methyl iodide.

In one embodiment, the halogen promoters are recovered and/or $C_{2+}$ alkyl halides are removed using an extractant. The extractant preferably is selected from the group consisting of $C_6$ to $C_{16}$ alkanes and combinations thereof. Preferably the extractant is hydrophobic and does not extract the PRC's. In some embodiments, the extractant is an $C_8$ to $C_{12}$ alkane. In some embodiments, the extractant is decane, dodecane, or combinations thereof.

PRC's are preferably removed with a PRC removal system (PRS) that comprises one or more distillation column. Exemplary PRS include those described in U.S. Pat. Nos. 7,223,886, 6,143,930 and 6,339,171, and US Pub. No. 2006/0247466, the entire contents and disclosures of which is hereby incorporated by reference. A stream enriched with PRC's may be separated from the acetic acid production process and introduced to the PRS. This stream may also comprise halogen promoters and/or $C_{2+}$ alkyl halides. In one embodiment, the halogen promoters may be recovered and/or $C_{2+}$ alkyl halides may be removed prior to introducing the stream to the PRS. Advantageously this embodiment removes the halogen promoters and $C_{2+}$ alkyl halides from the PRS and may improve the efficiency in removing the PRC's. In another embodiment, the halogen promoters may be recovered and/or $C_{2+}$ alkyl halides may be removed from one or more treated streams of the PRS. Generally these treated streams are purged from the system. Advantageously this embodiment removes the halogen promoters and $C_{2+}$ alkyl halides from the purge streams and may reduce costs for treating the purge streams.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort would be a routine undertaking for those of ordinary skill in the art having the benefit of this disclosure.

This invention relates to processes for the production of acetic acid and, in particular, to improved processes for the reduction and/or removal of permanganate reducing compounds (PRC's) formed during the carbonylation of methanol in the presence of a Group VIII metal carbonylation catalyst. PRC's, may include, for example, compounds such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. More specifically, this invention relates to improved processes for reducing and/or removing PRC's or their precursors from an acetic acid separation system that is used to purify a crude acetic acid product.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that rhodium is in the catalyst solution as an equilibrium mixture including $[Rh(CO)_2I_2]^-$ anion as is well known in the art. Iodide salts optionally maintained in the reaction mixtures of the processes described herein may be in the form of a soluble salt of an alkali metal or alkaline earth metal or a quaternary ammonium or phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. In some embodiments, the rhodium catalyst concentration in the liquid reaction medium may be in the range of 100 wppm to 6000 wppm. For additional detail regarding rhodium catalysis and iodide salt generation, see U.S. Pat. Nos. 5,001,259; 5,026,908; 5,144,068 and 7,005,541, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

Halogen promoters are generally used in combination with the Group VIII metal catalyst component. Methyl iodide is a preferred as the halogen promoter. Preferably, the concentration of halogen promoter in the liquid reaction composition is in the range 1 to 50% by weight, preferably 2 to 30% by weight.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction is preferably from 150° C. to 250° C., e.g., from 155° C. to 235° C., or from 160° C. to 220° C. The pressure of the carbonylation reaction is preferably from 10 to 200 bar, preferably 10 to 100 bar, most preferably 15 to 50 Bar. Acetic acid is typically manufactured in a liquid phase reaction at a temperature of from about 160-220° C. and a total pressure of from about 20 to about 50 bar.

The separation system preferably controls water and acetic acid content in the reactor, as well as throughout the system and, optionally, controls the removal of PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

Figure 2:
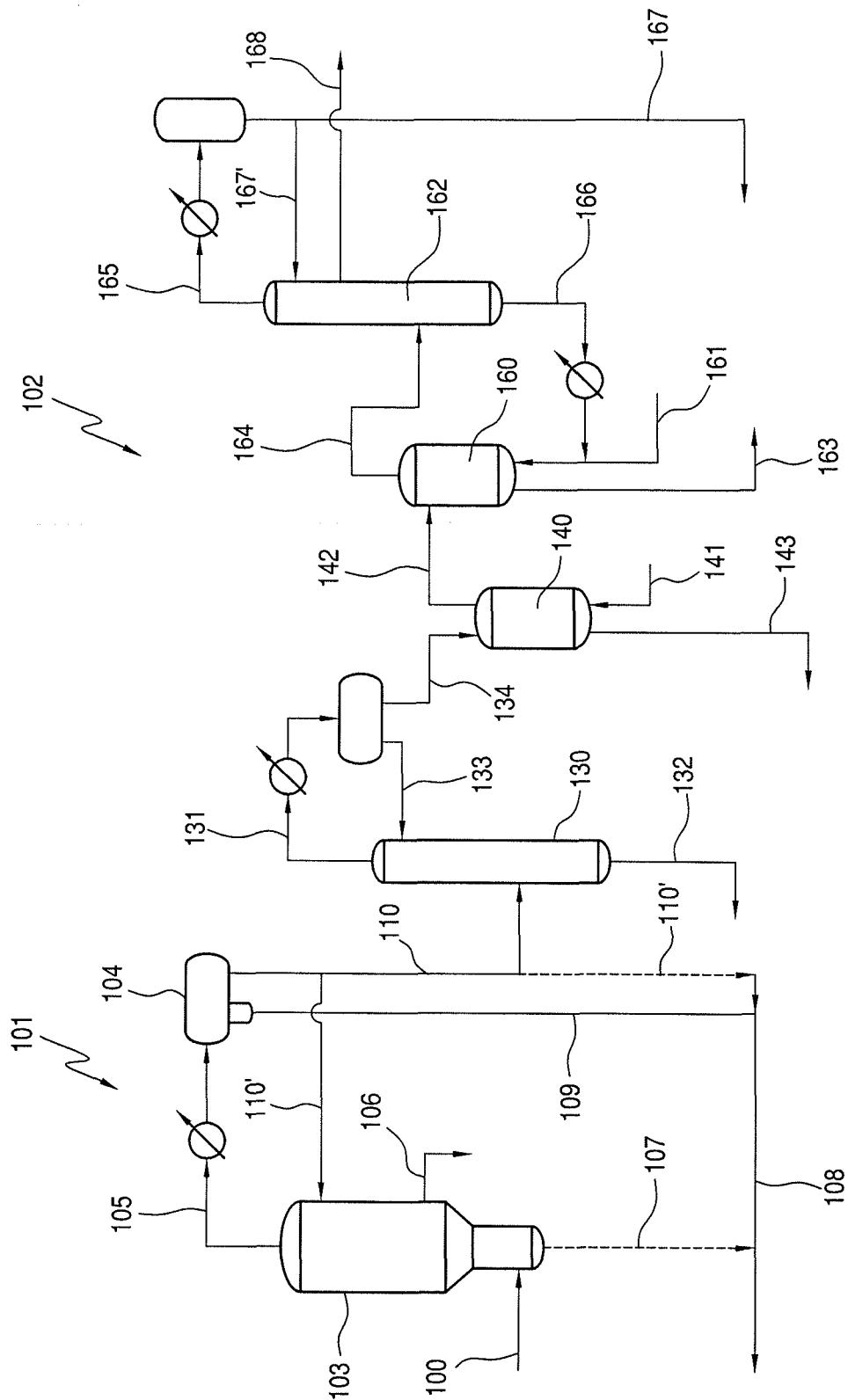
FIG. 2 illustrates an exemplary PRS that recovers halogen promoters from the aqueous stream of the PRS according to one embodiment of the invention.

Referring to FIGS. 1 and 2, a crude acetic acid product 100 is directed from a reaction section (not shown) comprising a reactor and a flasher to a purification section 101. Reaction sections for the production of acetic acid are known in the art, and are disclosed in U.S. Pat. Nos. 5,942,460; 5,932,764; 5,883,295; 5,877,348; 5,877,347 and 5,696,284, which are incorporated by reference in there entirety herein. Purification section 101 comprises PRC removal system (PRS) 102, light ends column 103 and overhead decanter 104. In further embodiments, the purification section 101 may comprise drying columns, guard beds, vent scrubbers, and/or heavy ends columns. Guard beds are described in U.S. Pat. Nos. 4,615,806, 4,894,477, and 6,225,498, the entire contents and disclosures of which are hereby incorporated by reference.

In light ends column 103, the crude acetic acid product 100 is separated into an overhead vapor stream 105, a purified acetic acid product that preferably is removed via a side stream 106, and an optional light ends residue stream 107. Acetic acid removed via side stream 106 preferably is subjected to further purification, such as in drying column (not shown) for selective separation of acetic acid from water and/or an optional heavy ends column (not shown), as described in U.S. Pat. No. 6,627,770, the entire contents and disclosures of which are hereby incorporated by reference, and optional guard beds (not shown). Optionally, a portion of the side stream 106 may be recirculated to the light ends column (not shown), preferably to a point below where side stream 106 was removed from light ends column, in order to improve the separation.

The light ends residue stream 107 typically will comprise heavy components, acetic acid, water, and entrained catalyst, it may be beneficial to recycle all or a portion of the light ends residue stream 107 to the process via recycle stream 108.

One or more recycle feed streams 108, may be fed to the reactor or anywhere else in the carbonylation process. Although one recycle feed stream 108 is shown in FIGS. 1 and 2, there may be multiple streams that are fed separately to the reactor and/or process. As discussed below the recycle feed streams 108 may comprise the components of the reaction medium, as well as residual and/or entrained catalyst and acetic acid.

The overhead vapor stream 105 comprises a halogen promoter; methyl acetate; hydrogen; water; methanol; PRC's; and acetic acid. It has been disclosed in U.S. Pat. Nos. 6,143,930 and 6,339,171 that there is generally a higher concentration of PRC's, and in particular acetaldehyde, in the overhead vapor stream 105 exiting the light ends column 103 than in the residue stream 107 exiting the light ends column 103.

The overhead vapor stream 105, is preferably condensed and directed to an overhead phase separation unit, as shown by overhead decanter 104. Conditions are desirably maintained in the process such that overhead vapor stream 105, once in decanter 104, will biphasically separate into a light phase and a heavy phase. Generally, the overhead vapor stream 105 is cooled to a temperature sufficient to condense and separate the halogen promoter, methyl acetate, PRC's, other carbonyl components and water into two phases. Non-condensable gases may be removed by a vent stream (not shown).

The condensed heavy phase in decanter 104 will generally comprise a halogen promoter, alkyl halides, methyl acetate, and PRC's. The condensed heavy liquid phase in the decanter 104 can be conveniently recirculated, either directly or indirectly, to the process via stream 109 and returned to the reaction section via recycle line 108.

The condensed light phase in decanter 104 preferably comprises water, acetic acid, and PRC's, as well as quantities of the halogen promoter, e.g., methyl iodide, methyl acetate, methanol, and/or alkyl iodides. The light phase exits decanter 104 via stream 110. A first portion, e.g., aliquot portion, of light phase stream is recycled to the top of the light ends column 103 as reflux stream 110'. A second portion, e.g., aliquot portion, of the light phase stream optionally may be recycled to reactor the as shown by recycle stream 110", when additional water is desired or needed in the reactor.

In accordance with a first embodiment of the present invention, also illustrated in FIG. 1, a portion of light phase stream 110 is directly or indirectly introduced to PRS 102. PRS 102 comprises an extractor 120, extractant feed 121, a removal column 122, distillation column 130, and optional extractor 140. In other embodiments, the PRS may comprise two or more distillation columns and one or more extractors. An exemplary two-stage distillation PRS comprising one or more extractors is described in U.S. Pat. No. 7,223,886, and is incorporated by reference in its entirety herein. An exemplary single stage PRS, similar to those shown in FIGS. 1 and 2, is described in U.S. Pub. No. 2006/0247466, and is incorporated by reference in its entirety herein.

In extractor 120, the halogen promoter and/or alkyl iodides are extracted from light phase stream 110 with an extractant, which is fed to the extractor 120 from extractant feed 121. The extractant preferably is selected from the group consisting of $C_6$ to $C_{16}$ alkanes and combinations thereof. As a result of this extraction, light phase 110 is separated into an aqueous stream 124 comprising methyl acetate, methanol, acetic acid, and at least one PRC, and a raffinate 123 comprising methyl acetate, the extractant and at least the halogen promoter and/or alkyl iodides. The alkyl iodides if present may be an alkyl iodide selected from the group consisting of ethyl iodide, propyl iodide, butyl iodide, pentyl iodide, hexyl iodide, and isomers and mixtures thereof.

Accordingly, it is desirable that the extraction be conducted at a combination of temperature and pressure such that the extractor contents can be maintained in the liquid state. Moreover, it is desirable to minimize the temperatures to which light phase stream 110 is exposed to minimize the likelihood of polymerization and condensation reactions involving acetaldehyde. In some embodiments, the extraction is conducted at a temperature of from 10° C. to 40° C.

Although the specific compositions of raffinate 123 may vary widely, it is preferred that a majority of the halogen promoters and/or alkyl iodides in the light phase in line 110 pass through to the raffinate 123. In one embodiment, at least 70% of the halogen promoters and/or alkyl iodides in the light phase in line 110 pass through to the raffinate 123, e.g., more preferably at least 85% or at least 95%. In a preferred embodiment, about 99% or more of the halogen promoters and/or alkyl iodides in the light phase in line 110 pass through to the raffinate 123. When methyl iodide is present in the light phase in line 110, at least 70% of the methyl iodide passes through to the raffinate 123, e.g., more preferably at least 85% or at least 95%. In addition, the raffinate 123 preferably comprises a low weight percent of PRC's, e.g., less than 10 wt. % of the total weight of the raffinate comprises PRC's, or more preferably less than 5 wt. %. In one embodiment, the raffinate 123 preferably comprises substantially no PRC's and the PRC's in the light phase 110 pass through the aqueous stream 124.

Raffinate 123 is directed to removal column 122 to produce a distillate stream 125 comprising halogen promoter, and a residue stream 126 comprising the extractant. Residue stream 126 is first cooled, and then may be recycled directly to extractor 120, or preferably is combined with extractant feed stream 121 and fed to extractor 120.

Distillate stream 125 is condensed and returned to the process via stream 127. At least a portion of the condensed distillate stream is refluxed back to the removal column via stream 127'. Distillate stream 125 primarily comprises halogen promoter, and may also comprise one or more alkyl iodides selected from the group consisting of ethyl iodide, propyl iodide, butyl iodide, pentyl iodide, hexyl iodide, and isomers and mixtures thereof.

In one additional embodiment, an alkyl halide purge stream (not shown) may be taken from removal column 122. Alkyl halide purge stream comprises halogen promoter and/or one or more $C_{2+}$ alkyl halides selected from the group consisting of ethyl iodide, propyl iodide, butyl iodide, pentyl iodide, hexyl iodide, and isomers and mixtures thereof. In some embodiments, alkyl halide purge stream may be directed to a holding tank and stored (not shown). Optionally, alkyl halide purge stream can be further processed to recover halogen promoter, wherein the halogen promoter is returned to the process.

Aqueous stream 124 from extractor 120 comprises primarily PRC's, methyl acetate, and methanol. Although the specific compositions of the aqueous stream 124 may vary widely, the aqueous stream 124 preferably comprises less than 10 wt. % of the halogen promoter and/or $C_{2+}$ alkyl halides, e.g., less than 5 wt. % or less than 1 wt. %. Without being bound by theory, the aqueous stream 124 has a reduced halogen promoter and/or alkyl halide concentration that advantageously allows for efficient PRC removal in the PRS 102 and an increased capacity for distillation column 130.

Aqueous stream 124 preferably is fed to distillation column 130 to produce an overhead PRC stream 131 and a bottoms stream 132. The overhead PRC stream 131 is enriched with PRC's, preferably acetaldehyde, with respect to bottoms stream 132. Overhead PRC stream 131 is deficient with methyl acetate, methanol, water and/or acetic acid, and more preferably deficient in all four, with respect to light phase 110. The bottoms stream 132 is enriched with methyl acetate, methanol, water and/or acetic acid (desirably all three) with respect to the overhead PRC stream 131. The bottoms stream 132 can be, and preferably is, recycled back to light ends column 103 via decanter 104 or via reflux line 110'.

As indicated above, the aqueous stream 124 fed to distillation column 130 contains little to no halogen promoters and/or $C_{2+}$ alkyl halides, and thus the overhead PRC stream 131 also contains little to no halogen promoters and/or $C_{2+}$ alkyl halides. In one embodiment, the overhead PRC stream comprises less than 10 wt. % of halogen promoters and/or $C_{2+}$ alkyl halides, e.g., less than 5 wt. % or less than 1 wt. %. In one embodiment, the overhead PRC stream 131 comprises less than 500 wppm of halogen promoters and/or $C_{2+}$ alkyl halides, e.g., less than 200 wppm or less than 100 wppm. In one embodiment, the overhead PRC stream 131 may be purged from the system without a water extraction.

As shown in FIG. 1, overhead PRC stream 131 is condensed and biphasically separated in decanter 134. A first portion of the condensed overhead PRC stream may be refluxed to distillation column 130 via line 133. A second portion of the condensed overhead PRC stream is purged from the system without any further treatment via line 135. Advantageously, this may reduce the processing of the line 135 to improve the efficiency of the system. In a preferred embodiment, the contents of line 135 contain substantially no halogen promoters and/or $C_{2+}$ alkyl halides, e.g., contains less than 1 wt. % or less than 0.5 wt. %.

In an optional embodiment, a third portion of the condensed overhead PRC stream may be fed to a water extractor 140 via line 136. The contents of line 136 are optionally chilled by passing through a cooler or chiller (not shown). PRC's may be extracted in extractor 140 in an aqueous purge stream 142. Purge stream 142 may be directed to a waste water treatment facilities. The raffinate 143 of extractor 140 may contain the halogen promoters along with low molecular weight alkanes. In some embodiments, raffinate 143 is further processed for iodine value. In one embodiment, $C_{2+}$ alkyl halides are preferably not returned to the reactor and removed from the system. Water used in extractor 140 may be obtained from an internal stream so as to maintain water balance within the reaction system.

In accordance with another embodiment of the present invention, as illustrated in FIG. 2, the light phase exits decanter 104 via stream 110. A first portion, e.g., aliquot portion, of light phase stream is recycled to the top of the light ends column 103 as reflux stream 110'. A second portion, e.g., aliquot portion, of the light phase stream optionally may be recycled to the reactor as shown by recycle stream 110", when additional water is desired or needed in the reactor.

In the embodiment depicted in FIG. 2, light phase stream 110 is directed to distillation column 130 to produce an overhead PRC stream 131 and a bottoms stream 132. The overhead PRC stream 131 is enriched with PRC's, preferably acetaldehyde and methyl iodide, with respect to bottoms stream 132. Overhead PRC stream 131 is deficient with methyl acetate, methanol, and/or acetic acid, and more preferably deficient in all three, with respect to light phase 110. The bottoms stream 132 is enriched with methyl acetate, methanol, and/or acetic acid (desirably all three) with respect to the overhead PRC stream 131. The bottoms stream 132 can be, and preferably is, recycled back to light ends column 103, either via decanter 104 or reflux line 110'. In one embodiment, the bottoms stream 132 comprises less than 500 wppm of halogen promoters and/or $C_{2+}$ alkyl halides, e.g., less than 200 wppm or less than 100 wppm.

A portion of overhead PRC stream 131 can be refluxed back to distillation column 130 via stream 133. A second portion of overhead PRC stream can be directed to a first extractor 140 via stream 134. The overhead PRC stream is extracted with a first extractant to produce a first raffinate 143 comprising a halogen promoter, methyl acetate, methanol and the first extractant, and an aqueous stream 142 comprising water, a halogen promoter, methanol, methyl acetate, and at least one PRC. The weight ratio of halogen promoters in the first raffinate to aqueous stream is 50:1 to 150:1, e.g., 80:1 to 120:1. In one embodiment, aqueous stream 142 may also comprise one or more $C_{2+}$ alkyl halides. The first extractant is fed to the first extractor 140 via first extractant feed stream 141. In some embodiments the first extractant is water. The first raffinate 143 may be recycled back to the process via recycle stream 108. In some embodiments, the first raffinate 143 is directed to decanter 104 or stream 109. In some embodiments, the first raffinate 143 is directed to a downstream distillation system (not shown).

In second extractor 160, the halogen promoter and/or alkyl iodides are extracted from the first aqueous stream 142 with a second extractant, which is fed to the second extractor 160 from second extractant feed 161. The second extractant preferably is different than the first extractant. The second extractant preferably is selected from the group consisting of $C_6$ to $C_{16}$ alkanes and combinations thereof. As a result of this extraction, first aqueous stream 142 is separated into a second raffinate stream 163 comprising water, and at least one PRC, and an extract stream 164 comprising the extractant and at least halogen promoter and/or alkyl iodides.

Accordingly, it is desirable that the extraction be conducted at a combination of temperature and pressure such that the extractor contents can be maintained in the liquid state. Moreover, it is desirable to minimize the temperatures to which first aqueous stream 142 is exposed to minimize the likelihood of polymerization and condensation reactions involving acetaldehyde. In some embodiments, extraction is conducted at a temperature of from 10° C. to 40° C.

Although the specific compositions of extract stream 164 may vary widely, it is preferred that a majority of the halogen promoters and/or alkyl iodides in the first aqueous phase in line 142 pass through to the extract stream 164. In one embodiment, at least 70% of the halogen promoters and/or alkyl iodides in the first aqueous stream in 142 pass through to the extract stream 164, e.g., more preferably at least 85% or at least 95%. In a preferred embodiment, about 99% or more of the halogen promoters and/or alkyl iodides in the first aqueous phase in line 142 pass through to the extract stream 164.

When methyl iodide is present in the first aqueous phase 142, at least 70% of the methyl iodide passes through to the extract stream 164, e.g., more preferably at least 85% or at least 95%. In addition, the extract stream 164 preferably comprises a low weight percent of PRC's, e.g., less than 10 wt. % of the total weight of the extract stream 164 comprises PRC's, or more preferably less than 5 wt. %. In one embodiment, the extract stream 164 preferably comprises substantially no PRC's and the PRC's in the first aqueous phase 142 pass through the second raffinate stream 163.

The second raffinate 163 is purged from the system where it can be disposed of as waste or further processed. In some embodiments, the second raffinate can be further processed into an acetaldehyde product. Second raffinate stream 163 from extractor 160 comprises primarily PRC's and methyl acetate, and water. Although the specific compositions of the aqueous stream 163 may vary widely, aqueous stream 163 preferably comprises less than 2 wt. % of the halogen promoter and/or $C_{2+}$ alkyl halides, e.g., less than 1 wt. % or less than 0.5 wt. %, or less than 0.1 wt. %. Extract stream 164 is directed to removal column 162 to produce a distillate stream 165 comprising halogen promoter and/or $C_{2+}$ alkyl halides, and a residue stream 166 comprising the second extractant. Residue stream 166 may be cooled and recycled directly to second extractor 160, or preferably is combined with second extractant feed stream 161 and fed to second extractor 160.

Distillate stream 165 is condensed and returned to the process via stream 167. In some embodiments, stream 167 is returned to the process via recycle stream 108, stream 109, decanter 104, stream 110", or stream 143. At least a portion of the condensed distillate stream is refluxed back to the removal column via stream 167'. Distillate stream 165 primarily comprises halogen promoter.

In some embodiments, an alkyl halide purge stream 168 can be taken from removal column 162. Alkyl halide purge stream 168 comprises one or more $C_{2+}$ alkyl halides selected from the group consisting of ethyl iodide, propyl iodide, butyl iodide, pentyl iodide, hexyl iodide, and isomers and mixtures thereof. In some embodiments, $C_{2+}$ alkyl halides purge stream 168 is directed to a holding tank and stored (not shown). Optionally, $C_{2+}$ alkyl halides purge stream 168 can be further processed to recover any halogen promoters or iodine value, such as HI, contained in the purge stream, wherein the halogen promoter or iodine value is returned to the process.

One of ordinary skill in the art having the benefit of this disclosure can design and operate the distillation columns described herein to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

In order that the invention disclosed herein may be more efficiently understood, examples are provided below. It should be understood that these examples are for illustrative purposes only and are not to be construed as limiting the invention in any manner.

EXAMPLES

Example 1

1 mL, of starting stream comprising methyl iodide and acetaldehyde was contacted with 1 mL, of the corresponding extractant at 25° C. The mixture was shaken five times and left for five minutes. The two phases were then separated and the resulting concentrations were determined by gas chromatography. This was conducted for three different concentrations, as shown below in Table 1.

TABLE 1

| | | Extractor 160 | | | | | |
| | | Conc. 1 (wt %) | | Conc. 2 (wt %) | | Conc. 3 (wt %) | |
| | Extractant | AcH | MeI | AcH | MeI | AcH | MeI |
| Starting Stream 142 | | 12.41 | 0.88 | 24.62 | 1.24 | 28.41 | 1.81 |
| Resulting Stream 164 | Pentane | 11.22 | 0.06 | 22.00 | 0.06 | 24.53 | 0.07 |
| | Hexane | 11.47 | 0.11 | 22.20 | 0.07 | 25.51 | 0.16 |
| | Octane | 11.20 | 0.07 | 23.27 | 0.09 | 26.80 | 0.09 |
| | Nonane | 11.85 | 0.13 | 22.77 | 0.05 | 25.73 | 0.08 |
| | Decane | 11.71 | 0.13 | 22.81 | 0.06 | 26.75 | 0.08 |
| | Dodecane | 11.90 | 0.08 | 22.20 | 0.05 | 26.02 | 0.08 |
| | Kerosene | 11.81 | 0.06 | 22.51 | 0.05 | 25.60 | 0.08 |

Example 2

The same procedure was followed as in Example 1, using concentration 3 from Table 1 above. The procedure was performed for three different ratios. As is shown in Table 2 below, Ratio 1 is 0.5 mL extractant contacted with 1 mL, of starting stream comprising methyl iodide and acetaldehyde. Ratio 2 is 1 mL extractant contacted with 1 mL starting stream comprising methyl iodide and acetaldehyde. Ratio 3 is 3 mL extractant contacted with 1 mL of starting stream comprising methyl iodide and acetaldehyde.

TABLE 2

| | | Extractor 160 | | | | | |
| | | Conc. (wt %) | | Conc. (wt %) | | Conc. (wt %) | |
| | | AcH | MeI | AcH | MeI | AcH | MeI |
| Starting Stream 142 | | 28.41 | 1.81 | 28.41 | 1.81 | 28.41 | 1.81 |
| | | Extractant:Starting Stream Ratio | | | | | |
| | Extractant | Ratio 1 (0.5:1) | | Ratio 2 (1:1) | | Ratio 3 (3:1) | |
| Resulting Stream 164 | Pentane | 26.82 | 0.12 | 24.53 | 0.07 | 21.52 | nd |
| | Hexane | 25.93 | 0.14 | 25.51 | 0.16 | 23.74 | nd |
| | Octane | 26.10 | 0.10 | 26.80 | 0.09 | 24.02 | nd |
| | Nonane | 25.60 | 0.08 | 25.73 | 0.08 | 24.09 | nd |
| | Decane | 25.34 | 0.09 | 26.75 | 0.08 | 24.09 | nd |
| | Dodecane | 25.73 | 0.13 | 26.02 | 0.08 | 24.36 | nd |
| | Kerosene | 26.42 | 0.10 | 25.60 | 0.08 | 24.42 | nd |

Example 3

The same procedure was followed as in Example 1, except that the starting stream is starting stream 110.

TABLE 3

| | | All 1:1 Starting stream:Extractant Extractor 120 | | | | |
|---|---|---|---|---|---|---|
| | Extractant | AcH | MeI | MeOH | MeOAc | HOAc |
| Starting Stream 110 | | 1.09 | 0.69 | 2.60 | 2.98 | 11.79 |
| Resulting Stream 124 | Pentane | 0.98 | 0.05 | 2.56 | 1.52 | 11.84 |
| | Hexane | 1.05 | 0.06 | 2.68 | 1.84 | 12.11 |
| | Octane | 0.99 | 0.06 | 2.56 | 1.85 | 12.03 |
| | Nonane | 1.01 | 0.06 | 2.60 | 1.94 | 12.09 |
| | Decane | 1.01 | 0.06 | 2.58 | 1.97 | 11.95 |
| | Dodecane | 1.02 | 0.06 | 2.59 | 1.97 | 12.07 |
| | Kerosene | 1.00 | 0.05 | 2.59 | 2.02 | 12.10 |

While the invention has been described in detail, modifications within the spirit and scope of the invention will be readily apparent to those of skill in the art. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for removing permanganate reducing compounds (PRC's) from a crude acetic acid composition, the process comprising the steps of:
    separating the crude acetic acid composition in a light ends column into an overhead vapor stream comprising halogen promoter, water, acetic acid, methyl acetate and at least one PRC, and an acetic acid product stream;
    condensing and biphasically separating the overhead vapor stream into a heavy phase and a light phase;
    separating the light phase in a distillation column into an overhead PRC stream and a bottoms stream, wherein the overhead PRC stream is enriched with PRC with respect to the bottoms stream;
    condensing the overhead PRC stream and extracting with a first extractant in a first extractor the condensed overhead PRC stream to obtain a first aqueous stream comprising water, halogen promoter and at least one PRC, and a first raffinate comprising methyl acetate; and
    extracting with a second extractant in a second extractor the first aqueous stream to obtain a second raffinate comprising water and at least one PRC, and an extract stream comprising halogen promoter, and the second extractant; wherein the second extractant comprises a $C_6$ to $C_{16}$ alkane.

2. The process of claim 1, wherein the first extractant and the second extractant are different.

3. The process of claim 1, wherein the second extractant comprises a $C_8$ to $C_{12}$ alkane.

4. The process of claim 1, wherein the second extractant comprises decane, dodecane, or mixtures thereof.

5. The process of claim 1, wherein the second raffinate comprises less than 500 wppm of halogen promoter.

6. The process of claim 1, wherein the second raffinate comprises less than 200 wppm of halogen promoter.

7. The process of claim 1, wherein the second raffinate comprises less than 100 wppm of halogen promoter.

8. The process of claim 1, wherein at least 70% of the halogen promoter in the first aqueous stream is extracted into the extract stream.

9. The process of claim 1, wherein at least 85% of the halogen promoter in the first aqueous stream is extracted into the extract stream.

10. The process of claim 1, wherein at least 95% of the halogen promoter in the first aqueous stream is extracted into the extract stream.

11. The process of claim 1, wherein the process further comprises:
    separating the extract stream in a recovery column to produce a residue comprising the second extractant, and a distillate comprising the halogen promoter; and
    introducing at least a portion of the distillate to a carbonylation reactor for producing the crude acetic acid composition.

12. The process of claim 11, wherein the distillate further comprises at least one alkyl iodide selected from the group consisting of ethyl iodide, propyl iodide, butyl iodide, pentyl iodide, hexyl iodide, and isomers and mixtures thereof.

13. The process of claim 12, wherein the process further comprises:
    directing a side stream from the recovery column to a holding vessel, wherein the side stream comprises the halogen promoter and the at least one $C_{2+}$ alkyl halides.

14. The process of claim 13, wherein the process further comprises:
    removing the halogen promoter from at least a portion of the side stream; and directing the halogen promoter to a process for producing acetic acid.

15. A process for removing permanganate reducing compounds (PRC's) from a crude acetic acid composition, the process comprising the steps of:
    separating the crude acetic acid composition in a distillation column to form a condensed heavy phase and a condensed light phase comprising halogen promoter, $C_{2+}$ alkyl halide and at least one PRC;
    separating the condensed light phase into an overhead PRC stream and a bottoms stream;
    condensing the overhead PRC stream and extracting in a first extractor with a first extractant the condensed overhead PRC stream to obtain a first aqueous stream comprising halogen promoter, $C_{2+}$ alkyl halide and at least one PRC, and a first raffinate comprising methyl acetate; and
    extracting in a second extractor with a second extractant the first aqueous stream to obtain a second raffinate comprising at least one PRC, and an extract stream comprising halogen promoter and $C_{2+}$ alkyl halide, wherein at least 70% of the halogen promoter and $C_{2+}$ alkyl halide present in the first aqueous stream is extracted into the extract stream; wherein the second extractant comprises a $C_6$ to $C_{16}$ alkane.

16. The process of claim 15, wherein the process further comprises:
    separating the extract stream to produce a distillate comprising halogen promoter and a residue comprising extractant; and
    recycling the distillate to a carbonylation reactor for producing the crude acetic acid composition.

17. The process of claim 15, wherein an overall $C_{2+}$ alkyl halide and halogen promoter recovery from the crude acetic acid composition is at least 70 wt. %.

18. The process of claim 15, wherein the extract stream comprises less than 10 wt. % PRC and greater than a minor amount of halogen promoter and $C_{2+}$ alkyl halide.

19. The process of claim 15, wherein the second raffinate comprises less than 10 wt. % halogen promoter and $C_{2+}$ alkyl halide and greater than a minor amount of PRC.

* * * * *